(12) United States Patent
Kim et al.

(10) Patent No.: US 7,501,424 B2
(45) Date of Patent: Mar. 10, 2009

(54) N-PHENYL-2-PYRIMIDINE-AMINE DERIVATIVES AND PROCESS FOR THE PREPARATION THEREOF

(75) Inventors: Dong-Yeon Kim, Seoul (KR); Dae-Jin Cho, Seoull (KR); Gong-Yeal Lee, Gyeonggi-Do (KR); Hong-Youb Kim, Seoul (KR); Seok-Hun Woo, Gyeonggi-do (KR); Yong-Seok Kim, Gyeonggi-Do (KR); Sun-Ahe Lee, Gyeonggi-Do (KR); Byoung-Cheol Han, Incheon (KR)

(73) Assignee: Il-Yang Pharm. Co., Ltd., Gyeonggi-do (KR)

( * ) Notice: Subject to any disclaimer, the term of this patent is extended or adjusted under 35 U.S.C. 154(b) by 0 days.

(21) Appl. No.: 11/813,175

(22) PCT Filed: Sep. 7, 2005

(86) PCT No.: PCT/KR2005/002962

§ 371 (c)(1),
(2), (4) Date: Sep. 18, 2007

(87) PCT Pub. No.: WO2007/018325

PCT Pub. Date: Feb. 15, 2007

(65) Prior Publication Data

US 2008/0096899 A1    Apr. 24, 2008

(30) Foreign Application Priority Data

Aug. 5, 2005 (KR) .................. 10-2005-0071656

(51) Int. Cl.
*C07D 239/28* (2006.01)
*A61K 31/505* (2006.01)

(52) U.S. Cl. .................. 514/255.05; 514/275; 544/295; 544/331

(58) Field of Classification Search .................. 544/295, 544/331; 514/255.05, 275
See application file for complete search history.

(56) References Cited

U.S. PATENT DOCUMENTS

| 6,368,651 B1 | 4/2002 | Gerlat et al. |
| 6,652,901 B2 | 11/2003 | Ishii |

FOREIGN PATENT DOCUMENTS

| WO | WO 02/24681 | 3/2002 |
| WO | WO 03/011836 | 2/2003 |
| WO | WO 2004/005281 | 1/2004 |
| WO | WO 2004/087699 | 10/2004 |

OTHER PUBLICATIONS

Manley et al., 2,4-Disubstituted Pyrimidines: A Novel Class of KDR Kinase Inhibitors, Bioorganic & Medicinal Chemistry letters, 2003, vol. 13, pp. 1673-1677.
Moffat et al., 4-Pyridin-5-yl-2 (3,4,5-trimethoxyphenylamino) Pyrimidines: Potent and Selective Inhibitors of ZAP 70, Bioorganic & Medicinal Chemistry letters, 1999, vol. 9, pp. 3351-3356.
Zimmermann et al., Potent and Selective Inhibitors of the Abl-kinase: Phenylamino-Pyrimidine (PAP) Derivatives, Bioorganic & Medicinal Chemistry Letters, 1997, vol. 7(2), pp. 187-192.
International Search Report, PCT/US 06/03526, Mar. 23, 2006.

*Primary Examiner*—Deepak Rao
(74) *Attorney, Agent, or Firm*—Howard M. Gitten; Edwards Angell Palmer & Dodge LLP (57) ABSTRACT

The present invention relates to a novel N-phenyl-2-pyrimidine-amine derivative represented by the above formula (1) and its salt showing a superior effect on cancer in warm-blooded animals, such as lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer, lymphoma, etc. The present invention also relates to a process for preparing the compound, and to a pharmaceutical composition for the treatment of the above various diseases, which comprises an effective amount of the compound as an active ingredient together with pharmaceutically acceptable inert carriers.

7 Claims, 1 Drawing Sheet

[Fig. 1]

N-PHENYL-2-PYRIMIDINE-AMINE DERIVATIVES AND PROCESS FOR THE PREPARATION THEREOF

This application is a 371 of PCT/KR05/02962 filed Sep. 7, 2005.

TECHNICAL FIELD

The present invention relates to a N-phenyl-2-pyrimidine-amine derivative represented by the following formula (1):

(1)

and its salt, in which $R_1$ represents optionally substituted thiazole, imidazole or pyrazine (wherein the substituent is amino group or lower alkyl);

$R_2$, $R_3$ and $R_6$ each independently represent hydrogen, halogen, lower alkyl or lower alkoxy;

$R_4$ and $R_5$ each independently represent hydrogen and $R_4$ and $R_5$ are not simultaneously hydrogen; or $R_4$ or $R_5$ each represents a radical having the following formula (2):

(2)

wherein $R_7$ represents lower alkyl or lower alkyl substituted with 1 to 3 halogen, $R_8$ represents aliphatic having 5 to 10 carbon atoms, or represents optionally substituted 5 to 7 membered saturated or unsaturated monocyclic radical (wherein the substituent is lower alkyl), or bi- or tri-cyclic radical optionally combined with a benzene ring (s), each of which has 1 to 3 hetero atoms selected from a group consisting of nitrogen, oxygen and sulfur, or represents piperazinyl or homopiperazinyl each of which is substituted by lower alkyl;

provided that $R_4$ represents a radical of formula (2), then at least one of $R_2$, $R_3$, $R_5$, and $R_6$ each independently represent hydrogen, halogen, lower alkyl or lower alkoxy; or provided that $R_5$ represents a radical of formula (2), then at least one of $R_2$, $R_3$, $R_4$, and $R_6$ each independently represent hydrogen, halogen, lower alkyl or lower alkoxy.

The present invention also relates to a process for preparing the compound of formula (1) and a pharmaceutical composition comprising an effective amount of the compound of formula (1) or salt thereof as an active ingredient together with pharmaceutically acceptable inert carriers.

BACKGROUND ART

The earlier therapeutic agent for Chronic Myelogenous Leukemia (CML, below), Imatinib mesylate (Gleevec, Korean Patent Laid-open Publication No. 1993-0021624 and Korean Patent Laid-open Publication No. 2001-0021950), has the structure of the above formula (1) wherein the amide type radical of the below formula (3) (n=0) is substituted at the position of $R_7$, $R_4$ is methyl, and $R_9$ is methylpiperazine, and so shows restrictive therapeutic effect, low stability, and several problems in its manufacturing process:

(3)

That is, since Imatinib mesylate has a high hygroscopic property, it may be easily deteriorated under the influence of the ambient moisture. Therefore, this compound should be recrystallized from a specific solvent such as methanol in order to maintain a specific crystal form, and should be used soon after its preparation. Further, this compound exhibits a therapeutic effect only on the CML and little effect on the other sites, differently from other anti cancer agents. It is synthesized in the order that 4-chloromethylbenzoic acid is combined first with N-methylpiperazine, chlorination is carried out using thionyl chloride, and the resulting side moiety is combined with the basic structure, wherein the use of thionyl chloride causes many problems such as generation of toxic gas, explosion, reduction of reaction yield, etc. Particularly, the stability of the intermediate adversely affect to the total yield of the compound.

DISCLOSURE OF INVENTION

Technical Problem

Thus, the present inventors have extensively and intensively studied to improve the problems as stated above. As a result, the inventors have identified that the novel compound of formula (1) as defined above exhibits a superior effect, and then completed the present invention.

Technical Solution

Therefore, a purpose of the present invention is to provide a N-phenyl-2-pyrimidine-amine derivative of the following formula (1):

(1)

and its salt, in which $R_1$ represents optionally substituted thiazole, imidazole or pyrazine (wherein the substituent is amino group or lower alkyl);

$R_4$ and $R_5$ each independently represent hydrogen, and $R_4$ and $R_5$ are not simultaneously hydrogen; or $R_4$ or $R_5$ each represents a radical having the following formula (2):

(2)

wherein $R_7$ represents lower alkyl or lower alkyl substituted with 1 to 3 halogen, $R_8$ represents aliphatic having 5 to 10 carbon atoms, or represents optionally substituted 5 to 7 membered saturated or unsaturated monocyclic radical (wherein the substituent is lower alkyl), or bi- or tri-cyclic radical optionally combined with a benzene ring (s), each of which has 1 to 3 hetero atoms selected from a group consisting of nitrogen, oxygen and sulfur, or represents piperazinyl or homopiperazinyl each of which is substituted by lower alkyl;

provided that $R_4$ represents a radical of formula (2), then at least one of $R_2$, $R_3$, $R_5$, and $R_6$ each independently represent hydrogen, halogen, lower alkyl or lower alkoxy; or provided that $R_5$ represents a radical of formula (2), then at least one of $R_2$, $R_3$, $R_4$, and $R_6$ each independently represent hydrogen, halogen, lower alkyl or lower alkoxy.

It is another purpose of the present invention to provide a process for preparing the compound of formula (1).

It is a further purpose of the present invention to provide a pharmaceutical composition for the treatment of cancer in warm-blooded animals, such as lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer, lymphoma, etc., which comprises an effective amount of the compound of formula (1) or salt thereof as an active ingredient together with pharmaceutically acceptable inert carriers.

It is a further purpose of the present invention to provide a method of treating cancer in warm-blooded animals, such as lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer, lymphoma, etc., which comprises having a host in need of such treatment ingest an amount of the compound of formula (1) or its salt as defined in claim 1 effective to provide such treatment.

Below, the present invention will be explained in more detail.

BEST MODE FOR CARRYING OUT THE INVENTION

In the above definitions for the substituents of N-phenyl-2-pyrimidine-amine derivative of formula (1), the term "lower alkyl" used alone or in a composite term with other terms preferably means straight-chain or branched and saturated aliphatic hydrocarbon radical having 1 to 6 carbon atoms such as methyl, ethyl, n-propyl, isopropyl, n-butyl, isobutyl, sec-butyl, t-butyl, pentyl, isoamyl, n-hexyl, etc., but does not limited thereto. The term "aliphatic" radical means alkenyl, alkynyl or alkyl. The term "lower alkoxy" used alone or in a composite term with other terms preferably has straight-chain or branched and saturated aliphatic hydrocarbon radical having 1 to 6 carbon atoms such as methoxy, ethoxy, n-propoxy, isopropoxy, n-butoxy, isobutoxy, sec-butoxy, t-butoxy, pentoxy, isopentoxy, n-hexoxy, etc., but does not limited thereto.

Preferable compounds among the compound of formula (1) include those wherein $R_1$ represents pyrazine, 2-methylpyrazine or thiazole;

$R_4$ or $R_5$ represents a radical having the following formula (2):

(2)

wherein $R_7$ represents trifluoromethyl or methyl, $R_8$ represents 2-methylimidazole, 4-methylimidazole, provided that $R_4$ represents a radical of formula (2), then at least one of $R_2$, $R_3$, $R_5$, and $R_6$ each independently represent hydrogen, halogen, lower alkyl or lower alkoxy; or provided that $R_5$ represents a radical of formula (2), then at least one of $R_2$, $R_3$, $R_4$, and $R_6$ each independently represent hydrogen, halogen, lower alkyl or lower alkoxy.

In the aspect of inhibition of protein kinase, particularly preferable compounds among the compound of formula (1) include those wherein $R_1$ represents pyrazine, 2-methylpyrazine or thiazole, $R_2$, $R_3$, $R_5$, $R_6$ each independently represent hydrogen, $R_4$ represents a radical of formula (2), $R_7$ represents trifluoromethyl or methyl, and $R_8$ represents 2-methylimidazole, 4-methylimidazole.

Further, the compound of formula (1) R1 represents pyrazine, 2-methylpyrazine or thiazole, R2 represents methyl, R3, R4, R6 each independently represent hydrogen, R5 represents a radical of formula (2), R7 represents trifluoromethyl or methyl, and R8 represents 2-methylimidazole, 4-methylimidazole is particularly preferable.

The compound of formula (1) includes one or more basic groups or one or more basic radicals, and so may form an acid addition salt with aliphatic sulfonic acid (i.e., methanesulfonic acid, ethanesulfonic acid), hydrochloric acid, sulfuric acid, phosphoric acid, trifluoroacetic acid, acetic acid, propionic acid, glycolic acid, succinic acid, maleic acid, fumaric acid, citric acid, tartaric acid, oxalic acid, amino acid (i.e., lysine), benzoic acid, salicylic acid, etc. When several basic groups exist in a molecule, the compound of formula (1) may form mono or poly acid addition salt. Among the pharmaceutically acceptable salts as mentioned above, acetic acid salt and hydrochloric acid salt are better than methanesulfonic acid salt, since they have better solubility in water and show good absorptivity in Pk test.

According to the present invention, the compound of formula (1) as defined above and its salt can be prepared by a process which comprises reacting a compound represented by the following formula (4a) or (4b):

wherein $R_1$ to $R_6$ are as defined above, with a compound represented by the following formula (5):

wherein $R_7$ to $R_8$ are as defined, to produce a compound represented by the following formula (1a) or (1b):

wherein $R_1$ to $R_8$ are as defined above. Therefore, it is another purpose of the present invention to provide the above process.

The above process according to the present invention is preferably carried out in a solvent and in the presence of a base. Any conventional solvent or base which does not adversely affect the reaction can be used, but one or more solvents selected from a group consisting of tetrahydrofuran, methylene chloride, ethanol, N,N-dimethylacetamide, ethylacetate, one or more bases selected from a group consisting of pyridine and triethylamine, sodium carbonate, potassium carbonate, sodium hydroxide, potassium hydroxide, sodium hydride can be preferably mentioned, and one or more catalysts selected from a group consisting of cupper, cupper iodide (II) and cupper oxide can be preferably mentioned.

The starting materials used in the above process according to the present invention are commercially available and can be easily obtained. The reaction may be conventionally carried out under cooling to warming. After the reaction is completed, the resulting product may be further purified by usual work-up processes, for example, column chromatography, recrystallization, etc.

The above process for preparing the compound of formula (1) of the present invention gives such advantages as stability of the chemical structure of the intermediates, simple control of reaction conditions, increase of the reaction yield, etc. when compared with the known process comprising the steps of coupling the compound of formula (4) with the compound of formula (5).

The compound of formula (1) of the present invention exhibits a superior effect on lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer, lymphoma, etc., and so can be advantageously used for the treatment of those diseases. Particularly, the compound of formula (1) shows better medicinal effect on CML than Imatinib mesylate, and the compound of formula (1) shows an excellent anti-cancer activity on several parts of the body including lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer, lymphoma, etc. Further, if the salt form of the compound of formula (1) is converted from methanesulfonate to acetate or hydrochloride, water solubility and absorptivity into the body of animals are highly increased. The effect of the compound of formula (1) and its salt according to the present invention can be confirmed by the test results of the following experiments.

When the active compound according to the present invention is used for clinical purpose, it is preferably administered in an amount ranging generally from 1 to 100 mg, preferably from 3 to 10 mg per kg of body weight a day. The total daily dosage may be administered once or over several times. However, the specific administration dosage for a patient can be varied with the specific compound used, body weight, sex or hygienic condition of the subject patient, diet, time or method of administration, excretion rate, mixing ratio of the agent, severity of the disease to be treated, etc.

The compound of the present invention may be administered in the form of injections or oral preparations.

Injections, for example, sterilized aqueous or oily suspension for injection, can be prepared according to the known procedure using suitable dispersing agent, wetting agent, or suspending agent. Solvents which can be used for preparing injections include water, Ringer's fluid, and isotonic NaCl solution, and also sterilized fixing oil may be conveniently used as solvent or suspending media. Any non-stimulative fixing oil including mono- or di-glyceride may be used for this purpose. Fatty acid such as oleic acid may also be used for injections.

As the solid preparations for oral administration, capsules, tablets, pills, powders, granules, etc., preferably capsules and tablets can be mentioned. It is also desirable for tablets and pills to be formulated into enteric-coated preparations. The solid preparations may be prepared by mixing the active compound of formula (1) according to the present invention with at least one carrier selected from a group consisting of inactive diluents such as sucrose, lactose, starch, etc., lubricants such as magnesium stearate, disintegrating agent, and binding agent.

When the compound according to the present invention is clinically applied for the treatment of lung cancer, gastric cancer, colon cancer, pancreatic cancer, hepatoma, prostatic cancer, breast cancer, chronic or acute leukemia, hematologic malignancy, encephalophyma, bladder cancer, rectal cancer, cervical cancer, lymphoma, etc., the active compound of formula (1) can be administered alone or in combination with the existing chemotherapeutic agents such as 5-Fu, cisplatin, taxol, methotrexate, anthracyclin, etc.

The present invention will be more specifically explained in the following Examples and Experiments. However, it should be understood that these Examples and Experiments are intended to illustrate the present invention but not in any manner to limit the scope of the present invention. In the following Examples, $R_f$ value was measured on silica gel (Merck, 60F254, Germany); the ratio of each solvent in the eluent mixture was volume ratio (v/v); and melting point was measured by DSC thermoanalysis instrument (NETZSCH, DSC204 cell). $^1$H-NMR was measured by Brucker, Ac-200.

EXAMPLES

Preparation 1

Preparation of 3-dimethylamino-1-thiazol-2-yl-propenone 2-acetylthiazole (35 g, 0.275 mol) and N,N-dimethylformamide dimethylacetal (55 ml, 0.412 mol) were added to a reaction vessel at room temperature (RT), and then heated and mixed at 70~80° C. for 4 hr. The mixture was cooled to RT, ether (30 ml) was added thereto, and the mixture was mixed for 1 hr under an ice-bath. The obtained orange color solid was filtered and then dried at RT to give the titled compound as yellow solid.

$^1$H-NMR (CDCl$_3$, δ)=3.01 (s, 3H), 3.22 (s, 3H), 6.13 (d, 1H), 7.56 (m, 1H), 7.93 (m, 2H)

Preparation 2

Preparation of 3-dimethylamino-1-pyrazin-2-yl-propenone 2-acetylpyrazine was used instead of 2-acetylthiazole according to the similar procedure to Preparation 1 to give the titled compound as yellow solid.

$^1$H-NMR (CDCl$_3$, δ)=2.99 (s, 3H), 3.19 (s, 3H), 6.34 (d, 1H), 7.95 (d, 1H), 8.55 (d, 1H), 8.63 (d, 1H), 9.31 (s, 1H)

Preparation 3

Preparation of 3-dimethylamino-1-(3-methylpyrazin-2-yl)-propenone 2-acetyl-3-methylpyrazine was used instead of 2-acetylthiazole according to the similar procedure to Preparation 1 to give the titled compound as brown solid.

$^1$H-NMR (CDCl$_3$, δ)=2.74 (s, 3H), 2.90 (s, 3H), 3.31 (s, 3H), 5.94 (d, 1H), 7.78 (d, 1H), 8.37 (s, 1H), 8.45 (d, 1H)

Preparation 4

Preparation of 3-dimethylamino-N-thiazol-2-yl-acrylamide

N-thiazol-2-yl-acetamide was used instead of 2-acetylthiazole according to the similar procedure to Preparation 1 to give the titled compound as yellow solid.

$^1$H-NMR (CDCl$_3$, δ)=2.45 (s, 3H), 2.48 (s, 3H), 5.37 (d, 1H), 6.85 (d, 1H), 7.36 (d, 1H), 8.21 (d, 1H), 9.35 (s, 1H)

Preparation 5

Preparation of 3-dimethylamino-1-imidazol-1-yl-propenone

N-acetylimidazole was used instead of 2-acetylthiazole according to the similar procedure to Preparation 1 to give the titled compound as brown solid.

$^1$H-NMR (CDCl$_3$, δ)=2.54 (s, 3H), 2.62 (s, 3H), 5.34 (d, 1H), 6.73 (d, 1H), 7.55 (d, 1H), 7.93 (d, 1H)

Preparation 6

Preparation of 4-guanidino-benzoic acid ethyl ester nitrate 4-aminobenzoic acid ethyl ester (20 g, 0.121 mol), nitric acid (7.26 g, 0.121 mol), cyanamide (50%, 14 ml 0.182 mol) were mixed under reflux with ethanol (50 ml). After 24 hr, the mixture was cooled to RT, and then washed with ethanol to give the titled compound as crystalline solid.

$^1$H-NMR (DMSO-d$_6$, δ)=1.32 (t, 3H), 4.32 (q, 2H), 7.35 (d, 2H), 7.98 (br, 3H), 9.93 (br, 1H)

Preparation 7

Preparation of 3-guanidino-4-methylbenzoic acid ethyl ester nitrate 3-amino-4-methylbenzoic acid ethyl ester was used instead of 4-aminobenzoic acid ethyl ester according to the similar procedure to Preparation 6 to give the titled compound as crystalline solid.

$^1$H-NMR (DMSO-d$_6$, δ)=1.30 (t, 3H), 2.27 (s, 3H), 4.22 (q, 2H), 7.22 (br, 3H), 7.31 (d, 1H), 7.75 (s, 1H), 7.82 (d, 1H), 9.38 (s, 1H)

Preparation 8

Preparation of 4-(4-pyridin-3-yl-pyrimidin-2-ylamino)benzoic acid ethyl ester 3-dimethylamino-1-pyridin-3-yl-propenone (3.3 g, 18.71 mmol), 4-guanidino-benzoic acid ethyl ester nitrate (5 g, 18.71 mmol) prepared in Preparation 6, sodium hydroxide (0.83 g, 20.58 mmol), and isopropanol (25 ml) were added to a reaction vessel, and then mixed under reflux. After 48 hr, a reaction vessel was cool to RT, an organic layer was extracted with ethyl acetate and water, distilled under vacuum, and then washed with ether to give the titled compound as yellow solid.

1H-NMR (CDCl3, δ)=1.34 (t, 3H), 4.30 (q, 2H), 7.63 (d, 2H), 7.97 (m, 4H), 8.70 (d, 1H), 8.80 (d, 1H), 8.85 (m, 1H), 9.38 (m, 1H), 10.27 (s, 1H)

Preparation 9

Preparation of 4-(4-thiazol-2-yl-pyrimidin-2-ylamino)benzoic acid ethyl ester 3-dimethylamino-1-thiazol-2-yl-propenone prepared in Preparation 1 was used instead of 3-dimethylamino-1-pyridin-3-yl-propenone according to the similar procedure to Preparation 8 to give the titled compound as yellow solid.

¹H-NMR (CDCl₃, δ)=1.32 (t, 3H), 4.24 (q, 2H), 7.52 (d, 2H), 7.94 (m, 5H), 8.05 (d, 1H), 8.66 (d, 1H), 10.29 (s, 1H)

Preparation 10

Preparation of 4-methyl-3-(4-thiazol-2-yl-pyrimidin-2-ylamino)benzoic acid ethyl ester 3-dimethylamino-1-thiazol-2-yl-propenone and 3-guanidino-4-methyl-benzoic acid ethyl ester nitrate prepared in Preparation 7 were used instead of 3-dimethylamino-1-pyridin-3-yl-propenone and 4-guanidino-benzoic acid ethyl ester nitrate according to the similar procedure to Preparation 8 to give the titled compound as yellow liquid.
1H-NMR (CDCl3, δ)=1.07 (t, 3H), 2.33 (s, 3H), 4.29 (q, 2H), 7.40 (m, 2H), 7.67 (d, 1H), 7.98 (d, 1H), 8.07 (d, 1H), 8.24 (s, 1H), 9.26 (s, 1H)

Preparation 11

Preparation of 4-methyl-3-(4-pyrazin-2-yl-pyrimidin-2-ylamino)benzoic acid ethyl ester 3-dimethylamino-1-pyrazin-2-yl-propenone prepared in Preparation 2 and 3-guanidino-4-methylbenzoic acid ethyl ester nitrate were used instead 3-dimethylamino-1-pyridin-3-yl-propenone and 4-guanidino-benzoic acid ethyl ester nitrate according to the similar procedure to Preparation 8 to give the titled compound as yellow solid.
1H-NMR (CDCl3, δ)=1.37 (t, 3H), 2.40 (s, 3H), 4.40 (q, 2H), 7.17 (s, 1H), 7.28 (d, 1H), 7.73 (m, 2H), 8.58 (d, 1H), 8.64 (d, 2H), 8.97 (s, 1H), 9.68 (s, 1H)

Preparation 12

Preparation of 4-(4-pyrazin-2-yl-pyrimidin-2-ylamino)benzoic acid ethyl ester 3-dimethylamino-1-pyrazin-2-yl-propenone was used instead of 3-dimethylamino-1-pyridin-3-yl-propenone according to the similar procedure to Preparation 8 to give the titled compound as yellow solid.
¹H-NMR (CDCl₃, δ)=1.27 (t, 3H), 4.36 (q, 2H), 6.60 (d, 1H), 6.63 (m, 2H), 7.74 (m, 2H), 8.12 (d, 1H), 8.87 (m, 3H), 9.88 (s, 1H)

Preparation 13

Preparation of 4-methyl-3-[4-(3-methylpyrazin-2-yl)-2-yl)-pyrimidin-2-ylamino]benzoic acid ethyl ester 3-dimethylamino-1-(3-methylpyrazin-2-yl)-propenone prepared in Preparation 3 was used instead of 3-dimethylamino-1-thiazol-2-yl-propenone according to the similar procedure to Preparation 10 to give the titled compound as yellow liquid.
1H-NMR (CDCl3, δ)=1.35 (t, 3H), 2.37 (s, 3H), 2.87 (s, 3H), 4.35 (q, 2H), 7.26 (t, 2H), 7.36 (d, 1H), 7.74 (m, 1H), 8.48 (s, 1H), 8.51 (m, 1H), 8.56 (m, 1H), 8.63 (s, 1H)

Preparation 14

Preparation of 4-[4-(3-methylpyrazin-2-yl)-pyrimidin-2-ylamino]benzoic acid ethyl ester 3-dimethylamino-1-(3-methylpyrazin-2-yl)-propenone was used instead of 3-dimethylamino-1-pyridin-3-yl-propenone according to the similar procedure to Preparation 8 to give the titled compound as yellow solid.
¹H-NMR (CDCl₃, δ)=1.29 (t, 3H), 2.53 (s, 3H), 4.65 (q, 2H), 7.37 (d, 2H), 7.77 (m, 2H), 8.62 (s, 1H), 8.64 (m, 1H), 8.58 (m, 2H), 8.99 (s, 1H)

Preparation 15

Preparation of 4-methyl-3-[4-(thiazol-2-ylamino)-pyrimidin-2-ylamino]benzoic acid ethyl ester 3-dimethylamino-N-thiazol-2-yl-acrylamide prepared in Preparation 4 was used instead of 3-dimethylamino-1-thiazol-2-yl-propenone according to the similar procedure to Preparation 10 to give the titled compound as yellow solid.
1H-NMR (CDCl3, δ)=1.26 (t, 3H), 2.14 (s, 3H), 5.22 (q, 2H), 7.24 (d, 2H), 7.32 (d, 1H), 7.46 (m, 3H), 8.03 (m, 2H), 8.53 (s, 1H), 9.25 (s, 1H)

Preparation 16

Preparation of 4-[4-(thiazol-2-ylamino)-pyrimidin-2-ylamino]benzoic acid ethyl ester 3-dimethylamino-N-thiazol-2-yl-acrylamide was used instead of 3-dimethylamino-1-pyridin-3-yl-propenone according to the similar procedure to Preparation 8 to give the titled compound as yellow solid.
¹H-NMR (CDCl₃, δ)=1.63 (t, 3H), 4.87 (q, 2H), 7.34 (d, 1H), 7.45 (d, 1H), 7.58 (m, 3H), 8.14 (m, 2H), 8.23 (d, 1H), 9.62 (s, 1H), 10.25 (s, 1H)

Preparation 17

Preparation of 3-(4-imidazol-1-yl-pyrimidin-2-ylamino)-4-methylbenzoic acid ethyl ester 3-dimethylamino-1-imidazol-1-yl-propenone prepared in Preparation 5 was used instead of 3-dimethylamino-1-thiazol-5-yl-propenone according to the similar procedure to Preparation 10 to give the titled compound as yellow solid.
1H-NMR (CDCl3, δ)=1.27 (t, 3H), 2.15 (s, 3H), 4.36 (q, 2H), 6.02 (d, 1H), 6.93 (d, 1H), 7.26 (m, 2H), 7.35 (m, 3H), 7.55 (d, 1H), 7.83 (s, 1H), 8.63 (s, 1H)

Preparation 18

Preparation of 4-(4-imidazol-1-yl-pyrimidin-2-ylamino)benzoic acid ethyl ester 3-dimethylamino-1-imidazol-1-yl-propenone was used instead of 3-dimethylamino-1-pyridin-3-yl-propenone according to the similar procedure to Preparation 8 to give the titled compound as yellow solid.
¹H-NMR (CDCl₃, δ)=1.33 (t, 3H), 4.36 (q, 2H), 6.03 (d, 1H), 6.93 (d, 1H), 7.33 (m, 2H), 7.42 (m, 2H), 7.64 (m, 2H), 7.89 (s, 1H), 8.77 (s, 1H)

Preparation 19

Preparation of 4-(4-pyridin-3-yl-pyrimidin-2-ylamino)-benzoic acid 4-(4-pyridin-3-yl-pyrimidin-2-ylamino)-benzoic acid ethyl ester prepared in Preparation 8 (19.6 g, 59.6 mmole) and 2N-sodium hydroxide (190 ml) were added to a reaction vessel under the solvent of water (190 ml) and ethanol (190 ml), mixed under reflux and cooled to RT, and pH thereof was adjusted to 1~2 with hydrochloride solution. The mixture was mixed for 1 hr, and filtered to give the titled compound as yellow solid.

$^1$H-NMR (DMSO-$d_6$, δ)=7.57 (m, 2H), 7.92 (q, 5H), 8.55 (d, 1H), 8.67 (d, 1H), 8.80 (s, 1H), 9.42 (br. 1H), 10.20 (s, 1H)

Preparation 20

Preparation of 4-(4-thiazol-2-yl-pyrimidin-2-ylamino)-benzoic acid 4-(4-thiazol-2-yl-pyrimidin-2-ylamino)-benzoic acid ethyl ester prepared in Preparation 9 was used instead of 4-(4-pyridin-3-yl-pyrimidin-2-ylamino)-benzoic acid ethyl ester according to the similar procedure to Preparation 19 to give the titled compound as yellow solid.

$^1$H-NMR (DMSO-$d_6$, δ)=7.54 (d, 1H), 7.93 (m, 4H), 8.05 (d, 1H), 8.11 (d, 1H), 8.7 (d, 1H), 10.30 (s, 1H), 12.34 (br, 1H)

Preparation 21

Preparation of 4-methyl-3-(4-thiazol-2-yl-pyrimidin-2-ylamino)-benzoic acid 4-methyl-3-(4-thiazol-2-yl-pyrimidin-2-ylamino)-benzoic acid ethyl ester prepared in Preparation 10 was used instead of 4-(4-pyridin-3-yl-pyrimidin-2-ylamino)-benzoic acid ethyl ester according to the similar procedure to Preparation 19 to give the titled compound as yellow solid.

$^1$H-NMR (DMSO-$d_6$, δ)=2.32 (s, 3H), 7.39 (m, 2H), 7.66 (m, 1H), 7.98 (d, 1H), 8.07 (d, 1H), 8.14 (s, 1H), 8.57 (d, 1H), 9.25 (s, 1H), 12.75 (s, 1H)

Preparation 22

Preparation of 4-methyl-3-(4-pyrazin-2-yl-pyrimidin-2-ylamino)-benzoic acid 4-methyl-3-(4-pyrazin-2-yl-pyrimidin-2-ylamino)-benzoic acid ethyl ester prepared in Preparation 11 was used instead of 4-(4-pyridin-3-yl-pyrimidin-2-ylamino)-benzoic acid ethyl ester according to the similar procedure to Preparation 19 to give the titled compound as yellow solid.

$^1$H-NMR (DMSO-$d_6$, δ)=2.34 (s, 3H), 7.33 (d, 1H), 7.63 (d, 2H), 8.33 (s, 1H), 8.59 (d, 1H), 8.74 (s, 2H), 9.12 (s. 1H), 9.42 (s, 1H)

Preparation 23

Preparation of 4-(4-pyrazin-2-yl-pyrimidin-2-ylamino)-benzoic acid 4-(4-pyrazin-2-yl-pyrimidin-2-ylamino)-benzoic acid ethyl ester prepared in Preparation 12 was used instead of 4-(4-pyridin-3-yl-pyrimidin-2-ylamino)-benzoic acid ethyl ester according to the similar procedure to Preparation 19 to give the titled compound as yellow solid.

$^1$H-NMR (DMSO-$d_6$, δ)=7.23 (m, 2H), 7.56 (d, 1H), 7.69 (s, 1H), 8.36 (m, 3H), 8.68 (m, 2H), 9.10 (s, 1H), 12.54 (br, 1H)

Preparation 24

Preparation of 4-methyl-3-[4-(3-methylpyrazin-2-yl)-pyrimidin-2-ylamino]benzoic acid 4-methyl-3-[4-(3-methylpyrazin-2-yl)-pyrimidin-2-ylamino]-benzoic acid ethyl ester prepared in Preparation 13 was used instead of 4-(4-pyridin-3-yl-pyrimidin-2-ylamino)-benzoic acid ethyl ester according to the similar procedure to Preparation 19 to give the titled compound as yellow solid.

$^1$H-NMR (DMSO-$d_6$, δ)=2.31 (s, 3H), 2.64 (s, 3H), 7.30 (d, 2H), 7.64 (d, 1H), 8.12 (s, 1H), 8.55 (m, 3H), 9.07 (s, 1H), 12.75 (br, 1H)

Preparation 25

Preparation of 4-[4-(3-methyl-pyrazin-2-yl)-pyrimidin-2-ylamino]-benzoic acid

4-[4-(3-methylpyrazin-2-yl)-pyrimidin-2-ylamino]-benzoic acid ethyl ester prepared in Preparation 14 was used instead of 4-(4-pyridin-3-yl-pyrimidin-2-ylamino)-benzoic acid ethyl ester according to the similar procedure to Preparation 19 to give the titled compound as yellow solid.

$^1$H-NMR (DMSO-$d_6$, δ)=1.85 (s, 3H), 7.36 (d, 2H), 7.44 (s, 1H), 7.65 (d, 1H), 8.15 (s, 1H), 8.56 (m, 3H), 9.12 (s, 1H), 12.67 (br, 1H)

Preparation 26

Preparation of 4-methyl-3-[4-(thiazol-2-ylamino)-pyrimidin-2-ylamino]-benzoic acid 4-methyl-3-[4-(thiazol-2-ylamino)-pyrimidin-2-ylamino]-benzoic acid ethyl ester prepared in Preparation 15 was used instead of 4-(4-pyridin-3-yl-pyrimidin-2-ylamino)-benzoic acid ethyl ester according to the similar procedure to Preparation 19 to give the titled compound as yellow solid.

$^1$H-NMR (DMSO-$d_6$, δ)=1.85 (s, 3H), 7.36 (d, 2H), 7.44 (s, 1H), 7.65 (d, 1H), 8.15 (s, 1H), 8.56 (m, 3H), 9.12 (s, 1H), 12.67 (br, 1H)

Preparation 27

Preparation of 4-[4-(thiazol-2-ylamino)-pyrimidin-2-ylamino]-benzoic acid

4-[4-(thiazol-2-ylamino)-pyrimidin-2-ylamino]-benzoic acid ethyl ester prepared in Preparation 16 was used instead of 4-(4-pyridin-3-yl-pyrimidin-2-ylamino)-benzoic acid ethyl ester according to the similar procedure to Preparation 19 to give the titled compound as yellow solid.

$^1$H-NMR (DMSO-$d_6$, δ)=6.03 (s, 1H), 6.68 (m, 2H), 7.05 (s, 1H), 7.35 (d, 1H), 7.77 (m, 2H), 8.21 (s, H), 9.82 (s, 1H), 10.24 (s, 1H)

Preparation 28

Preparation of 3-(4-imidazol-1-yl-pyrimidin-2-ylamino)-4-methylbenzoic acid 3-(4-imidazol-1-yl-pyrimidin-2-ylamino)-4-methylbenzoic acid ethyl ester prepared in Preparation 17 was used instead of 4-(4-pyridin-3-yl-pyrimidin-2-ylamino)-benzoic acid ethyl ester according to the similar procedure to Preparation 19 to give the titled compound as yellow solid.

$^1$H-NMR (DMSO-$d_6$, δ)=2.38 (s, 3H), 6.24 (d, 1H), 7.12 (d, 1H), 7.34 (m, 3H), 7.49 (m, 2H), 7.69 (s, 1H), 8.95 (s, 1H)

Preparation 29

Preparation of 4-(4-imidazol-1-yl-pyrimidin-2-ylamino)-benzoic acid 4-(4-imidazol-1-yl-pyrimidin-2-ylamino)-benzoic acid ethyl ester prepared in Preparation 18 was used instead of 4-(4-pyridin-3-yl-pyrimidin-2-ylamino)-benzoic acid ethyl ester according to the similar procedure to Preparation 19 to give the titled compound as yellow solid.

$^1$H-NMR (DMSO-d$_6$, δ)=6.32 (d, 1H), 6.96 (m, 2H), 7.32 (d, 1H), 7.56 (d, 1H), 7.89 (m, 2H), 8.12 (m, 2H), 9.32 (s, 1H)

Preparation 30

Preparation of 3-(4-methyl-imidazol-1-yl)-5-trifluoromethyl-phenylamine 3-amino-5-bromo-benzotrifluoride (17.1 g, 71.24 mmol), 4-methylimidazole (17.6 g, 213.72 mmol), potassium carbonate (9.8 g, 71.24 mmol), cupper (1.1 g, 17.81 mmol), and cupper iode (II) (3.4 g, 17.81 mmol) were added to N,N-dimethylacetamide (100 ml) at room temperature, and mixed therewith at 140~150° C. for 16 hr. After the reaction was completed, the temperature of the reaction vessel was cooled to RT. Then, ethyl acetate (200 ml) was added thereto and mixed therewith for 30 min. The reaction mixture was filtered with Celite, and an organic layer of the filtered solution was washed with water, dried with magnesium sulfate, distilled under vacuum, and washed with n-hexane to give the titled compound as pale white solid.

$^1$H-NMR (CDCl$_3$, δ)=2.28 (s, 3H), 4.04 (br, 2H), 6.79 (s, 1H), 6.83 (s, 1H), 6.92 (s, 1H), 7.00 (s, 1H), 7.77 (s, 1H)

Preparation 31

Preparation of 3-(2-methyl-imidazol-1-yl)-5-trifluoromethyl-phenylamine 2-methylimidazole was used instead of 3-amino-5-bromo-benzotrifluoride and 4-methylimidazole according to the similar procedure to Preparation 30 to give the titled compound as yellow solid.

$^1$H-NMR (CDCl3, δ)=2.36 (s, 3H), 4.17 (br, 2H), 6.69 (s, 1H), 6.86 (s, 1H), 6.91 (s, 1H), 7.02 (s, 1H), 7.26 (s, 1H)

Example 1

Preparation of N-[3-(4-methylimidazol-1-yl)-5-trifluoromethyl-phenyl]-4-(4-pyridin-3-yl-pyrimidin-2-ylamino)-benzamide 4-(4-pyridin-3-yl-pyrimidin-2-ylamino)-benzoic acid prepared in Preparation 19 (242 mg, 0.83 mmol) and 3-(4-methyl-imidazol-1-yl)-5-trifluoromethyl-phenylamine prepared in Preparation 30 (200 mg, 0.83 mmol), N,N-dimethyl formamide (10 ml), and diethylcyano phosphate (0.245 ml, 1.658 mmol) were added to a reaction vessel, and cooled to 10° C. Triethylamine (0.231 ml, 1.658 mmol) was added thereto. After 30 min, the mixture was mixed at 60° C. for 15 hr. The mixture was cooled to RT, and an organic layer was obtained with the solution of ethyl acetate and sodium bi carbonate, concentrated under vacuum, and subjected to column chromatography (5:1/CHCl$_3$:MeOH) to give the titled compound as pale yellow solid.

$^1$H-NMR (DMSO-d$_6$, δ)=2.20 (s, 3H), 7.39 (s, 1H), 7.56 (d, 2H), 8.03 (m, 5H), 8.17 (s, 1H), 8.21 (d, 1H), 8.32 (s, 1H), 8.49 (d, 2H), 8.63 (d, 1H), 8.72 (d, 1H), 9.36 (s, 1H), 10.15 (s, 1H); 10.48 (s, 1H)

Example 2

Preparation of N-[3-(2-methylimidazol-1-yl)-5-trifluoromethyl-phenyl]-4-(4-pyridin-3-yl-pyrimidin-2-ylamino)-benzamide 3-(2-methyl-imidazol-1-yl)-5 -trifluoromethyl-phenylamine prepared in Preparation 31 was used instead of 3-(4-methyl-imidazol-1-yl)-5-trifluoromethyl-phenylamine and 4-(4-pyridin-3-yl-pyrimidin-2-ylamino)-benzoic acid prepared in Preparation 19 according to the similar procedure to Example 1 to give the titled compound as pale white solid.

$^1$H-NMR (DMSO-d$_6$, δ)=2.25 (s, 3H), 7.32 (s, 1H), 7.55 (d, 2H), 8.05 (m, 5H), 8.21 (s, 1H), 8.26 (d, 1H), 8.37 (s, 1H), 8.50 (d, 2H), 8.64 (d, 1H), 8.78 (d, 1H), 9.42 (s, 1H), 10.25 (s, 1H), 11.21 (s, 1H)

Example 3

Preparation of N-[3-(4-methylimidazol-1-yl)-5-trifluoromethyl-phenyl]-4-(4-thiazol-2-yl-pyrimidin-2-ylamino)-benzamide 4-(4-thiazol-2-yl-pyrimidin-2-ylamino)-benzoic acid prepared in Preparation 20 was used instead of 4-(4-pyridin-3-yl-pyrimidin-2-ylamino)-benzoic acid according to the similar procedure to Example 1 to give the titled compound as pale white solid.

$^1$H-NMR (DMSO-d$_6$, δ)=2.21 (s, 3H), 7.43 (m, 1H), 7.56 (m, 1H), 7.65 (m, 1H), 8.06 (m, 7H), 8.19 (m, 2H), 8.71 (d, 1H), 10.29 (s, 1H), 10.52 (s, 1H)

Example 4

Preparation of N-[3-(2-methylimidazol-1-yl)-5-trifluoromethyl-phenyl]-4-(4-thiazol-2-yl-pyrimidin-2-ylamino)-benzamide 3-(2-methylimidazol-1-yl)-5-trifluoromethyl-phenylamine was used instead of 3-(4-methylimidazol-1-yl)-5-trifluoromethyl-phenylamine according to the similar procedure to Example 3 to give the titled compound as pale white solid.

$^1$H-NMR (DMSO-d$_6$, δ)=2.23 (s, 3H), 7.42 (m, 1H), 7.55 (m, 1H), 7.68 (m, 1H), 8.07 (m, 7H), 8.20 (m, 2H), 8.73 (d, 1H), 10.31 (s, 1H), 10.55 (s, 1H)

Example 5

Preparation of 4-methyl-N-[3-(4-methylimidazol-1-yl)-5-trifluoromethyl-phenyl]-3-(4-thiazol-2-yl-pyrimidin-2-ylamino)-benzamide 4-methyl-3-(4-thiazol-2-yl-pyrimidin-2-ylamino)-benzoic acid prepared in Preparation 21 was used instead of 4-(4-pyridin-3-yl-pyrimidin-2-ylamino)-benzoic acid according to the similar procedure to Example 1 to give the titled compound as pale yellow solid.

$^1$H-NMR (DMSO-d$_6$, δ)=2.19 (s, 3H), 2.36 (s, 3H), 7.24 (s, 1H), 7.35 (m, 2H), 7.47 (s, 1H), 7.64 (d, 1H), 7.71 (d, 1H), 7.92 (d, 1H), 8.01 (s, 1H), 8.11 (s, 1H), 8.30 (s, 2H), 8.47 (d, 1H), 9.00 (s, 1H), 10.49 (s, 1H)

Example 6

Preparation of 4-methyl-N-[3-(2-methylimidazol-1-yl)-5-trifluoromethyl-phenyl]-3-(4-thiazol-2-yl-pyrimidin-2-ylamino)-benzamide 3-(2-methylimidazol-1-yl)-5-trifluoromethyl-phenylamine was used instead of 3-(4-methylimidazol-1-yl)-5-trifluoromethyl-phenylamine according to the similar procedure to Example 5 to give the titled compound.

$^1$H-NMR (DMSO-$d_6$, δ)=2.20 (s, 3H), 2.38 (s, 3H), 7.25 (s, 1H), 7.42 (m, 2H), 7.47 (s, 1H), 7.68 (d, 1H), 7.73 (d, 1H), 7.96 (d, 1H), 8.06 (s, 1H), 8.15 (s, 1H), 8.35 (s, 2H), 8.51 (d, 1H), 9.23 (s, 1H), 10.52 (s, 1H)

Example 7

Preparation of 4-methyl-N-(5-methylthiazol-2-yl)-3-(4-thiazol-2-yl-pyrimidin-2-ylamino)-benzamide 4-methyl-3-(4-thiazol-2-yl-pyrimidin-2-ylamino)-benzoic acid and 2-amino-5-methylthiazole were used instead of 4-(4-pyridin-3-yl-pyrimidin-2-ylamino)-benzoic acid and 3-(4-methylimidazol-1-yl)-5-trifluoromethyl-phenylamine according to the similar procedure to Example 5 to give the titled compound as yellow brown solid.

$^1$H-NMR (DMSO-$d_6$, δ)=2.32 (s, 3H), 2.36 (s, 3H), 7.19 (s, 1H), 7.44 (d, 2H), 7.85 (d, 1H), 7.95 (s, 1H), 8.06 (s, 1H), 8.31 (s, 1H), 8.58 (d, 1H), 9.29 (s, 1H), 12.36 (s, 1H)

Example 8

Preparation of 4-methyl-N-[3-(4-methylimidazol-1-yl)-5-trifluoromethyl-phenyl]-3-(4-pyrazin-2-yl-pyrimidin-2-ylamino)-benzamide 4-methyl-3-(4-pyrazin-2-yl-pyrimidin-2-ylamino)-benzoic acid prepared in Preparation 22 was used instead of 4-(4-pyridin-3-yl-pyrimidin-2-ylamino)-benzoic acid according to the similar procedure to Example 1 to give the titled compound as pale yellow solid.

$^1$H-NMR (DMSO-$d_6$, δ)=2.21 (s, 3H), 2.38 (s, 3H), 7.35 (s, 1H), 7.39 (s, 1H), 7.54 (s, 1H), 7.63 (d, 1H), 7.75 (d, 1H), 8.14 (d, 2H), 8.38 (d, 2H), 8.54 (d, 2H), 8.68 (s, 1H), 9.06 (s, 1H), 9.45 (s, 1H), 10.56 (s, 1H)

Example 9

Preparation of 4-methyl-N-[3-(2-methylimidazol-1-yl)-5-trifluoromethyl-phenyl]-3-(4-pyrazin-2-yl-pyrimidin-2-ylamino)-benzamide 4-methyl-3-(4-pyrazin-2-yl-pyrimidin-2-ylamino)-benzoic acid was used instead of 4-(4-pyridin-3-yl-pyrimidin-2-ylamino)-benzoic acid according to the similar procedure to Example 2 to give the titled compound as pale yellow solid.

$^1$H-NMR (DMSO-$d_6$, δ)=2.35 (s, 3H), 2.37 (s, 3H), 6.95 (s, 1H), 7.37 (s, 1H), 7.41 (s, 1H), 7.51 (s, 1H), 7.65 (d, 1H), 7.78 (d, 1H), 8.18 (s, 1H), 8.35 (d, 2H), 8.63 (d, 2H), 8.75 (s, 1H), 9.27 (s, 1H), 9.41 (s, 1H), 10.68 (s, 1H)

Example 10

Preparation of N-[3-(4-methylimidazol-1-yl)-5-trifluoromethyl-phenyl]-4-(4-pyrazin-2-yl-pyrimidin-2-ylamino)-benzamide 4-(4-pyrazin-2-yl-pyrimidin-2-ylamino)-benzoic acid prepared in Preparation 23 was used instead of 4-(4-pyridin-3-yl-pyrimidin-2-ylamino)-benzoic acid according to the similar procedure to Example 1 to give the titled compound as pale yellow solid.

$^1$H-NMR (DMSO-$d_6$, δ)=2.20 (s, 3H), 7.35 (s, 1H), 7.61 (m, 1H), 8.07 (s, 3H), 8.19 (d, 2H), 8.36 (s, 1H), 8.43 (d, 1H), 8.57 (d, 2H), 9.29 (s, 1H), 10.12 (s, 1H), 10.42 (s, 1H)

Example 11

Preparation of N-[3-(2-methylimidazol-1-yl)-5-trifluoromethyl-phenyl]-4-(4-pyrazin-2-yl-pyrimidin-2-ylamino)-benzamide 3-(2-methylimidazol-1-yl)-5-trifluoromethyl-phenylamine was used instead of 3-(4-methylimidazol-1-yl)-5-trifluoromethyl-phenylamine according to the similar procedure to Example 10 to give the titled compound as pale yellow solid.

$^1$H-NMR (DMSO-$d_6$, δ)=2.34 (s, 3H), 2.29 (d, 2H), 7.52 (m, 3H), 7.94 (s, 3H), 8.03 (d, 2H), 8.40 (d, 1H), 8.51 (d, 2H), 9.17 (s, 1H), 10.09 (s, 1H), 10.39 (s, 1H)

Example 12

Preparation of 4-methyl-N-[3-(4-methylimidazol-1-yl)-5-trifluoromethyl-phenyl]-3-[4-(3-methylpyrazin-2-yl)-pyrimidin-2-ylamino]-benzamide 4-methyl-3-[4-(3-methylpyrazin-2-yl)-pyrimidin-2-ylamino]-benzoic acid prepared in Preparation 24 was used instead of 4-(4-pyridin-3-yl-pyrimidin-2-ylamino)-benzoic acid according to the similar procedure to Example 1 to give the titled compound as pale yellow solid.

$^1$H-NMR (DMSO-$d_6$, δ)=2.22 (s, 3H), 2.39 (s, 3H), 2.79 (s, 3H), 7.06 (s, 1H), 7.20 (s, 1H), 7.32 (s, 3H), 7.59 (d, 2H), 8.18 (s, 1H), 8.50 (m, 3H), 8.58 (s, 1H), 8.92 (s, 1H)

Example 13

Preparation of 4-methyl-N-[3-(2-methylimidazol-1-yl)-5-trifluoromethyl-phenyl]-3-[4-(3-methylpyrazin-2-yl)-pyrimidin-2-ylamino]-benzamide 3-(2-methylimidazol-1-yl)-5-trifluoromethyl-phenylamine was used instead of 3-(4-methylimidazol-1-yl)-5-trifluoromethyl-phenylamine according to the similar procedure to Example 12 to give the titled compound as pale yellow solid.

$^1$H-NMR (DMSO-$d_6$, δ)=2.39 (s, 3H), 2.43 (s, 3H), 2.80 (s, 3H), 7.08 (d, 1H), 7.26 (s, 1H), 7.33 (m, 3H), 7.61 (d, 1H), 8.10 (d, 2H), 8.50 (d, 2H), 8.56 (d, 1H), 8.64 (s, 1H), 9.16 (s, 1H)

Example 14

Preparation of N-[3-(4-methylimidazol-1-yl)-5-trifluoromethyl-phenyl]-4-[4-(3-methylpyrazin-2-yl)-pyrimidin-2-ylamino]-benzamide 4[4-(3-methylpyrazin-2-yl)-pyrimidin-2-ylamino]-benzoic acid prepared in Preparation 25 was used instead of 4-(4-pyridin-3-yl-pyrimidin-2-ylamino)-benzoic acid according to the similar procedure to Example 1 to give the titled compound as pale yellow solid.

$^1$H-NMR (DMSO-$d_6$, δ)=2.24 (s, 3H), 2.75 (s, 3H), 2.21 (s, 1H), 7.54 (m, 3H), 7.92 (m, 3H), 8.07 (d, 2H), 8.24 (s, 1H), 8.36 (d, 1H), 8.42 (d, 2H), 9.37 (s, 1H), 9.98 (s, 1H)

Example 15

Preparation of N-[3-(2-methylimidazol-1-yl)-5-trifluoromethyl-phenyl]-4-[4-(3-methylpyrazin-2-yl)-pyrimidin-2-ylamino]-benzamide 3-(2-methylimidazol-1-yl)-5-trifluoromethyl-phenylamine was used instead of 3-(4-methylimidazol-1-yl)-5-trifluoromethyl-phenylamine according to the similar procedure to Example 14 to give the titled compound as pale yellow solid.

$^1$H-NMR (DMSO-$d_6$, δ)=2.36 (s, 3H), 2.79 (s, 3H), 7.17 (d, 2H), 7.31 (m, 3H), 7.64 (m, 3H), 7.92 (d, 2H), 8.15 (d, 1H), 8.29 (d, 2H), 9.12 (s, 1H), 9.62 (s, 1H)

Example 16

Preparation of 4-methyl-N-[3-(4-methylimidazol-1-yl)-5-trifluoromethyl-phenyl]-3-[4-(thiazol-2-ylamino)-pyrimidin-2-ylamino]-benzamide 4-methyl-3-[4-(thiazol-2-ylamino)-pyrimidin-2-ylamino]-benzoic acid prepared in Preparation 26 was used instead of 4-(4-pyridin-3-yl-pyrimidin-2-ylamino)-benzoic acid according to the similar procedure to Example 1 to give the titled compound as pale yellow solid.

$^1$H-NMR (DMSO-$d_6$, δ)=2.19 (s, 3H), 2.35 (s, 3H), 7.02 (d, 1H), 7.15 (s, 1H), 7.24 (s, 1H), 7.32 (s, 1H), 7.56 (m, 3H), 7.97 (d, 2H), 8.40 (s, 1H), 8.52 (d, 1H), 8.67 (s, 1H), 9.00 (s, 1H), 9.54 (s, 1H), 10.49 (s, 1H)

Example 17

Preparation of 4-methyl-N-[3-(2-methylimidazol-1-yl)-5-trifluoromethyl-phenyl]-3-[4-(thiazol-2-ylamino)-pyrimidin-2-ylamino]-benzamide 3-(2-methylimidazol-1-yl)-5-trifluoromethyl-phenylamine was used instead of 3-(4-methylimidazol-1-yl)-5-trifluoromethyl-phenylamine according to the similar procedure to Example 16 to give the titled compound as pale yellow solid.

$^1$H-NMR (DMSO-$d_6$, δ)=2.31 (s, 3H), 2.39 (s, 3H), 6.99 (d, 1H), 7.08 (s, 1H), 7.12 (d, 2H), 7.25 (s, 1H), 7.43 (m, 3H), 7.72 (d, 2H), 8.41 (d, 1H), 8.51 (s, 1H), 9.12 (s, 1H), 9.37 (s, 1H), 10.41 (s, 1H)

Example 18

Preparation of N-[3-(4-methylimidazol-1-yl)-5-trifluoromethyl-phenyl]-4-[4-(thiazol-2-ylamino)-pyrimidin-2-ylamino]-benzamide 4-[4-(thiazol-2-ylamino)-pyrimidin-2-ylamino]-benzoic acid prepared in Preparation 27 was used instead of 4-(4-pyridin-3-yl-pyrimidin-2-ylamino)-benzoic acid according to the similar procedure to Example 1 to give the titled compound as yellow brown solid.

$^1$H-NMR (DMSO-$d_6$, δ)=2.24 (s, 3H), 6.92 (d, 1H), 7.13 (s, 1H), 7.27 (s, 1H), 7.51 (d, 2H), 7.89 (m, 3H), 7.96 (d, 2H), 8.29 (s, 1H), 8.30 (d, 1H), 9.58 (s, 1H), 8.96 (s, 1H), 9.38 (s, 1H), 10.16 (s, 1H)

Example 19

Preparation of N-[3-(2-methylimidazol-1-yl)-5-trifluoromethyl-phenyl]-4-[4-(thiazol-2ylamino)-pyrimidin-2-ylamino]-benzamide 3-(2-methylimidazol-1-yl)-5-trifluoromethyl-phenylamine was used instead of 3-(4-methylimidazol-1-yl)-5-trifluoromethyl-phenylamine according to the similar procedure to Example 18 to give the titled compound as pale yellow solid.

1H-NMR (DMSO-d6, δ)=2.26 (s, 3H), 7.05 (d, 1H), 7.10 (s, 1H), 7.24 (d, 2H), 7.46 (d, 2H), 7.69 (m, 3H), 7.89 (d, 2H), 8.24 (d, 1H), 8.65 (s, 1H), 9.16 (s, 1H), 9.43 (s, 1H), 10.27 (s, 1H)

Example 20

Preparation of 3-(4-imidazol-1-yl-pyrimidin-2-ylamino)-4-methyl-N-[3-(4-methylimidazol-1-yl)-5-trifluoromethyl-phenyl]-benzamide 3-(4-imidazol-1-yl-pyrimidin-2-ylamino)-4-methylbenzoic acid prepared in Preparation 28 was used instead of 4-(4-pyridin-3-yl-pyrimidin-2-ylamino)-benzoic acid according to the similar procedure to Example 1 to give the titled compound as pale yellow solid.

$^1$H-NMR (DMSO-$d_6$, δ)=2.27 (s, 3H), 2.30 (s, 3H), 6.84 (d, 1H), 7.24 (s, 1H), 7.39 (s, 1H), 7.56 (d, 2H), 7.89 (m, 3H), 7.92 (d, 2H), 8.07 (s, 1H), 8.35 (s, 1H), 8.42 (d, 1H), 9.40 (s, 1H), 9.89 (s, 1H)

Example 21

Preparation of 3-(4-imidazol-1-yl-pyrimidin-2-ylamino)-4-methyl-N-[3-(2-methylimidazol-1-yl)-5-trifluoromethyl-phenyl]-benzamide 3-(2-methylimidazol-1-yl)-5-trifluoromethyl-phenylamine was used instead of 3-(4-methylimidazol-1-yl)-5-trifluoromethyl-phenylamine according to the similar procedure to Example 20 to give the titled compound as pale yellow solid.

$^1$H-NMR (DMSO-$d_6$, δ)=2.29 (s, 3H), 2.35 (s, 3H), 6.96 (d, 1H), 7.15 (d, 2H), 7.30 (s, 1H), 7.59 (m, 3H), 7.74 (d, 2H), 7.88 (d, 2H), 8.32 (s, 1H), 8.39 (d, 1H), 9.37 (s, 1H), 10.15 (s, 1H)

Example 22

Preparation of 4-(4-imidazol-1-yl-pyrimidin-2-ylamino)-N-[3-(4-methylimidazol-1-yl)-5-trifluoromethyl-phenyl]-benzamide 4-(4-imidazol-1-yl-pyrimidin-2-ylamino)-benzoic acid prepared in Preparation 29 was used instead of 4-(4-pyridin-3-yl-pyrimidin-2-ylamino)-benzoic acid according to the similar procedure to Example 1 to give the titled compound as pale yellow solid.

$^1$H-NMR (DMSO-$d_6$, δ)=2.24 (s, 3H), 6.92 (d, 1H), 7.30 (s, 1H), 7.43 (d, 2H), 7.49 (d, 2H), 7.76 (m, 3H), 7.87 (d, 2H), 8.21 (s, 1H), 8.25 (s, 1H), 8.29 (s, 1H), 9.45 (s, 1H), 10.02 (s, 1H)

Example 23

Preparation of 4-(4-imidazol-1-yl-pyrimidin-2-ylamino)-N-[3-(2-methylimidazol-1-yl)-5-trifluoromethyl-phenyl]-benzamide 3-(2-methylimidazol-1-yl)-5-trifluoromethyl-phenylamine was used instead of 3-(4-methylimidazol-1-yl)-5-trifluoromethyl-phenylamine according to the similar procedure to Example 22 to give the titled compound as pale yellow solid.
$^1$H-NMR (DMSO-$d_6$, δ)=2.26 (s, 3H), 7.04 (d, 1H), 7.28 (d, 2H), 7.48 (d, 2H), 7.52 (d, 2H), 7.64 (m, 3H), 7.81 (d, 2H), 8.30 (s, 1H), 8.33 (d, 1H), 8.47 (s, 1H), 10.09 (s, 1H)

Example 24

Preparation of N-[3-(4-methylimidazol-1-yl)-5-trifluoromethyl-phenyl]-4-(4-pyridin-3-yl-pyrimidin-2-ylamino)-benzamide 2 hydrochloride N-[3-(4-methylimidazol-1-yl)-5-trifluoromethyl-phenyl]-4-(4-pyridin-3-yl-pyrimidin-2-ylamino)-benzamide (100 mg, 0.19 mmol) prepared in Example 1 was added to acetone (20 ml), and the mixture was cooled to 0° C. A mixture of HCl (35%, 42.5□, 0.41 mmol) and acetone (5 ml) was dropwisely added thereto. The mixture was mixed at room temperature for 18 hr, and filtered to give the titled compound as yellow brown solid.
$^1$H-NMR (DMSO-$d_6$, δ)=2.25 (s, 3H), 7.34 (s, 1H), 7.55 (d, 2H), 8.09 (m, 5H), 8.17 (s, 1H), 8.27 (d, 1H), 8.35 (s, 1H), 8.54 (d, 2H), 8.63 (d, 1H), 8.75 (d, 1H), 9.52 (s, 1H), 10.69 (s, 1H)

Example 25

Preparation of N-[3-(2-methylimidazol-1-yl)-5-trifluoromethyl-phenyl]-4-(4-pyridin-3-yl-pyrimidin-2-ylamino)-benzamide 2 hydrochloride N-[3-(2-methylimidazol-1-yl)-5-trifluoromethyl-phenyl]-4-(4-pyridin-3-yl-pyrimidin-2-ylamino)-benzamide prepared in Example 2 was used instead of N-[3-(4-methylimidazol-1-yl)-5-trifluoromethyl-phenyl]-4-(4-pyridin-3-yl-pyrimidin-2-yl amino)-benzamide according to the similar procedure to Example 24 to give the titled compound as yellow brown solid.
$^1$H-NMR (DMSO-$d_6$, δ)=2.32 (s, 3H), 7.37 (s, 1H), 7.62 (d, 2H), 8.14 (m, 5H), 8.26 (s, 1H), 8.31 (d, 1H), 8.39 (s, 1H), 8.51 (d, 2H), 8.71 (d, 1H), 8.83 (d, 1H), 8.47 (s, 1H), 10.37 (s, 1H)

Example 26

Preparation of 4-methyl-N-[3-(4-methylimidazol-1-yl)-5-trifluoromethyl-phenyl]-3-(4-pyrazin-2-yl-pyrimidin-2-ylamino)-benzamide 2 hydrochloride 4-methyl-N-[3-(4-methylimidazol-1-yl)-5-trifluoromethyl-phenyl]-3-(4-pyrazin-2-yl-pyrimidin-2-ylamino)-benzamide prepared in Example 8 was used instead of N-[3-(4-methylimidazol-1-yl)-5-trifluoromethyl-phenyl]-4-(4-pyridin-3-yl-pyrimidin-2-yl amino)-benzamide according to the similar procedure to Example 24 to give the titled compound as yellow brown solid.
$^1$H-NMR (DMSO-$d_6$, δ)=2.29 (s, 6H), 7.31 (s, 1H), 7.35 (s, 1H), 7.57 (s, 1H), 7.61 (d, 1H), 7.54 (d, 2H), 8.41 (d, 2H), 8.56 (d, 2H), 8.76 (s, 1H), 9.27 (s, 1H), 9.78 (s, 1H) 10.87 (s, 1H)

Example 27

Preparation of 4-methyl-N-[3-(2-methylimidazol-1-yl)-5-trifluoromethyl-phenyl]-3-(4-pyrazin-2-yl-pyrimidin-2-ylamino)-benzamide 2 hydrochloride 4-methyl-N-[3-(2-methylimidazol-1-yl)-5-trifluoromethyl-phenyl]-3-(4-pyrazin-2-yl-pyrimidin-2-ylamino)-benzamide prepared in Example 9 was used instead of N-[3-(4-methylimidazol-1-yl)-5-trifluoromethyl-phenyl]-4-(4-pyridin-3-yl-pyrimidin-2-ylamino)- benzamide according to the similar procedure to Example 24 to give the titled compound as yellow brown solid.
$^1$H-NMR (DMSO-$d_6$, δ)=2.30 (s, 6H), 7.12 (s, 1H), 7.32 (s, 1H), 7.45 (s, 1H), 7.49 (s, 1H), 7.67 (d, 1H), 7.82 (d, 1H), 8.23 (s, 1H), 8.35 (d, 2H), 8.67 (d, 2H), 8.98 (s, 1H), 9.37 (s, 1H), 9.65 (s, 1H), 10.82 (s, 1H)

Example 28

Preparation of 4-methyl-N-[3-(4-methylimidazol-1-yl)-5-trifluoromethyl-phenyl]-3-(4-thiazol-2-yl-pyrimidin-2-ylamino)-benzamide 2 hydrochloride 4-methyl-N-[3-(4-methylimidazol-1-yl)-5-trifluoromethyl-phenyl]-3-(4-thiazol-2-yl-pyrimidin-2-ylamino)-benzamide prepared in Example 5 was used instead of N-[3-(4-methylimidazol-1-yl)-5-trifluoromethyl-phenyl]-4-(4-pyridin-3-yl-pyrimidin-2-yl amino)-benzamide according to the similar procedure to Example 24 to give the titled compound as yellow brown solid.
$^1$H-NMR (DMSO-$d_6$, δ)=2.21 (s, 6H), 7.19 (s, 1H), 7.39 (m, 2H), 7.49 (s, 1H), 7.71 (s, 1H), 7.79 (d, 1H), 7.97 (d, 1H), 8.09 (s, 2H), 8.21 (s, 1H), 8.35 (s, 2H), 8.51 (d, 1H), 9.24 (s, 1H), 10.37 (s, 1H)

Example 29

Preparation of 4-methyl-N-[3-(2-methylimidazol-1-yl)-5-trifluoromethyl-phenyl]-3-(4-thiazol-2-yl-pyrimidin-2-ylamino)-benzamide 2 hydrochloride 4-methyl-N-[3-(2-methylimidazol-1-yl)-5-trifluoromethyl-phenyl]-3-(4-thiazol-2-yl-pyrimidin-2-ylamino)-benzamide prepared in Example 6 was used instead of N-[3-(4-methylimidazol-1-yl)-5-trifluoromethyl-phenyl]-4-(4-pyridin-3-yl-pyrimidin-2-yl amino)-benzamide according to the similar procedure to Example 24 to give the titled compound as yellow brown solid.
$^1$H-NMR (DMSO-$d_6$, δ)=2.23 (s, 6H), 7.27 (s, 1H), 7.39 (m, 2H), 7.46 (s, 1H), 7.72 (d, 1H), 7.79 (d, 1H), 8.02 (d, 1H), 8.10 (s, 1H), 8.19 (s, 1H), 8.42 (s, 2H), 8.56 (d, 1H), 9.39 (s, 1H), 10.84 (s, 1H)

Example 30

Preparation of N-[3-(4-methylimidazol-1-yl)-5-trifluoromethyl-phenyl]-4-(4-thiazol-2-yl-pyrimidin-2-ylamino)-benzamide 2 hydrochloride N-[3-(4-methylimidazol-1-yl)-5-trifluoromethyl-phenyl]-4-(4-thiazol-2-yl-pyrimidin-2-ylamino)-benzamide prepared in Example 3 was used instead of N-[3-(4-methylimidazol-1-yl)-5-trifluoromethyl-phenyl]-4-(4-pyridin-3-yl-pyrimidin-2-yl amino)-benzamide according to the similar procedure to Example 24 to give the titled compound as yellow brown solid.

¹H-NMR (DMSO-d₆, δ)=2.26 (s, 3H), 7.39 (s, 1H), 7.51 (d, 2H), 7.61 (s, 1H), 7.69 (d, 1H), 7.74 (s, 1H), 8.05 (s, 1H), 8.13 (m, 3H), 8.19 (s, 1H), 8.25 (d, 1H), 8.83 (d, 1H), 10.40 (s, 1H), 10.79 (s, 1H)

Example 31

Preparation of N-[3-(2-methylimidazol-1-yl)-5-trifluoromethyl-phenyl]-4-(4-thiazol-2-yl-pyrimidin-2-ylamino)-benzamide 2 hydrochloride N-[3-(2-methylimidazol-1-yl)-5-trifluoromethyl-phenyl]-4-(4-thiazol-2-yl-pyrimidin-2-ylamino)-benzamide prepared in Example 4 was used instead of N-[3-(4-methylimidazol-1-yl)-5-trifluoromethyl-phenyl]-4-(4-pyridin-3-yl-pyrimidin-2-yl amino)-benzamide according to the similar procedure to Example 24 to give the titled compound as yellow brown solid.

¹H-NMR (DMSO-d₆, δ)=2.22 (s, 3H), 7.29 (d, 1H), 7.38 (d, 2H), 7.47 (d, 2H), 7.53 (d, 1H), 7.68 (m, 3H), 7.92 (d, 2H), 8.35 (d, 1H), 8.74 (d, 1H), 10.21 (s, 1H), 10.49 (s, 1H)

Example 32

Preparation of N-[3-(2-methylimidazol-1-yl)-5-trifluoromethyl-phenyl]-4-[4-(2-methylimidazol-1-yl)-pyrimidin-2-ylamino]-benzamide 3-(2-methylimidazol-1-yl)-5-trifluoromethyl-phenylamine prepared in Preparation 31 and 4-[4-(2-methylimidazol-1-yl)pyrimidin-2-amino]benzoic acid were used according to the similar procedure to Example 1 to give the titled compound as yellow solid.

¹H-NMR (DMSO-d₆, δ)=2.26 (s, 3H), 2.75 (s, 3H), 7.03 (d, 1H), 7.25 (d, 2H), 7.47 (d, 2H), 7.52 (d, 1H), 7.65 (m, 3H), 7.80 (d, 2H), 7.81 (d, 1H), 8.34 (d, 1H), 8.45 (s, 1H), 10.08 (s, 1H)

Example 33

Preparation of N-[3-(4-methylimidazol-1-yl)-5-trifluoromethyl-phenyl]-4-[4-(2-methylimidazol-1-yl)-pyrimidin-2-ylamino]-benzamide 3-(4-methylimidazol-1-yl)-5-trifluoromethyl-phenylamine prepared in Example 30 was used instead of 3-(2-methylimidazol-1-yl)-5-trifluoromethyl-phenylamine according to the similar procedure to Example 32 to give the titled compound as yellow solid.

¹H-NMR (DMSO-d₆, δ)=2.23 (s, 3H), 2.76 (s, 3H), 6.92 (d, 1H), 7.31 (d, 1H), 7.44 (d, 2H), 7.48 (d, 2H), 7.77 (m, 3H), 7.88 (d, 2H), 8.20 (s, 1H), 8.27 (s, 1H), 8.30 (s, 1H), 9.43 (s, 1H), 10.03 (s, 1H)

Example 34

Preparation of 4-methyl-N-[3-(2-methylimidazol-1-yl)-5-trifluoromethyl-phenyl]-3-[4-(2-methylimidazol-1-yl)-pyrimidin-2-ylamino]-benzamide 4-methyl-3-[4-(2-methylimidazol-1-yl)pyrimidin-2-amino]benzoic acid and 3-(2-methylimidazol-1-yl)-5-trifluoromethyl-phenylamine prepared in Preparation 31 were used according to the similar procedure to Example 1 to give the titled compound as yellow solid.

¹H-NMR (DMSO-d₆, δ)=2.29 (s, 3H), 2.33 (s, 3H), 2.77 (s, 3H), 6.95 (d, 1H), 7.15 (d, 2H), 7.31 (s, 1H), 7.60 (m, 3H), 7.75 (d, 2H), 7.89 (d, 2H), 8.33 (s, 1H), 8.40 (d, 1H), 9.39 (s, 1H), 10.15 (s, 1H)

Example 35

Preparation of 4-methyl-N-[3-(4-methylimidazol-1-yl)-5-trifluoromethyl-phenyl]-3-[4-(2-methylimidazol-1-yl)-pyrimidin-2-ylamino]-benzamide 3-(4-methylimidazol-1-yl)-5-trifluoromethyl-phenylamine prepared in Preparation 30 was used instead of 3-(2-methylimidazol-1-yl)-5-trifluoromethyl-phenylamine according to the similar procedure to Example 34 to give the titled compound as yellow solid.

¹H-NMR (DMSO-d₆, δ)=2.27 (s, 3H), 2.31 (s, 3H), 2.71 (s, 3H), 6.85 (d, 1H), 7.25 (s, 2H), 7.39 (s, 1H), 7.57 (d, 2H), 7.88 (m, 3H), 7.93 (d, 2H), 8.08 (s, 1H), 8.37 (d, 1H), 8.43 (d, 1H), 9.41 (s, 1H), 9.88 (s, 1H)

Example 36

Preparation of N-[3-(2-methylimidazol-1-yl)-5-trifluoromethyl-phenyl]-4-[4-(4-methylimidazol-1-yl)-pyrimidin-2-ylamino]-benzamide 4-[4-(4-methylimidazol-1-yl)pyrimidin-2-amino]benzoic acid and 3-(2-methylimidazol-1-yl)-5-trifluoromethyl-phenylamine prepared in Preparation 31 were used according to the similar procedure to Example 1 to give the titled compound as yellow solid.

¹H-NMR (DMSO-d₆, δ)=2.25 (s, 3H), 2.77 (s, 3H), 7.02 (d, 1H), 7.27 (d, 2H), 7.48 (d, 2H), 7.53 (d, 2H), 7.66 (m, 3H), 7.81 (d, 2H), 8.32 (s, 1H), 8.33 (d, 1H), 8.45 (s, 1H), 10.07 (s, 1H)

Example 37

Preparation of N-[3-(4-methylimidazol-1-yl)-5-trifluoromethyl-phenyl]-4-[4-(4-methylimidazol-1-yl)-pyrimidin-2-ylamino]-benzamide 3-(4-methylimidazol-1-yl)-5-trifluoromethyl-phenylamine prepared in Preparation 30 was used instead of 3-(2-methylimidazol-1-yl)5-trifluoromethyl-phenylamine according to the similar procedure to Example 36 to give the titled compound as yellow solid.

¹H-NMR (DMSO-d₆, δ)=2.22 (s, 3H), 2.75 (s, 3H), 6.93 (d, 1H), 7.32 (s, 1H), 7.45 (d, 2H), 7.47 (s, 2H), 7.78 (m, 3H), 7.89 (d, 2H), 8.21 (s, 1H), 8.28 (s, 1H), 8.31 (s, 1H), 9.45 (s, 1H), 10.01 (s, 1H)

Example 38

Preparation of 4-methyl-N-[3-(2-methylimidazol-1-yl)-5-trifluoromethyl-phenyl]-3[4-(4-methylimidazol-1-yl)-pyrimidin-2-ylamino]-benzamide 4-methyl-3-[4-(4-methylimidazol-1-yl)pyrimidin-2-ylamino]benzoic acid and 3-(2-methylimidazol-1-yl)-5-trifluoromethyl-phenylamine prepared in Preparation 31 were used according to the similar procedure to Example 1 to give the titled compound as yellow solid.

¹H-NMR (DMSO-d₆, δ)=2.27 (s, 3H), 2.34 (s, 3H), 2.75 (s, 3H), 6.97 (d, 1H), 7.17 (d, 2H), 7.30 (s, 1H), 7.61 (m, 3H), 7.77 (d, 2H), 7.88 (d, 2H), 8.33 (s, 1H), 8.41 (d, 1H), 9.38 (s, 1H), 10.17 (s, 1H)

Example 39

Preparation of 4-methyl-N-[3-(4-methylimidazol-1-yl)-5-trifluoromethyl-phenyl]-43-[4-(4-methylimidazol-1-yl)-pyrimidin-2-ylamino]-benzamide 3-(4-methylimidazol-1-yl)-5-trifluoromethyl-phenylamine prepared in Preparation 30 was used instead of 3-(2-methylimidazol-1-yl)-5-trifluoromethyl-phenylamine according to the similar procedure to Example 38 to give the titled compound as yellow solid.

$^1$H-NMR (DMSO-$d_6$, δ)=2.26 (s, 3H), 2.32 (s, 3H), 2.71 (s, 3H), 6.88 (d, 1H), 7.27 (s, 1H), 7.40 (s, 1H), 7.57 (d, 2H), 7.88 (m, 3H), 7.95 (d, 2H), 8.10 (s, 1H), 8.39 (s, 1H), 8.45 (d, 1H), 9.43 (s, 1H), 9.90 (s, 1H)

Experiment 1

In the present experiment, the inhibitory activity of the compound of formula (1) was determined against the growth of K562 cancer cell. First, the cells were allowed to stand in RPMI (Roswell Park Memorial Institute)-1640 medium containing 10% (v/v) fetal bovine serum in an incubator of 37° C. and 5% by volume of $CO_2$. The cancer cells (1000 cells) were transferred to a 96-well plate, and the test compound was diluted. The plate was allowed to stand under the above mentioned conditions for 2 days. After this treatment, to the cells was added 0.2% MTT (3-[4,5-dimethylthiazol-2-yl]-2,5-diphenyltetrazolium bromide) solution, and the resulting mixture was allowed to stand under the constant temperature-condition for 4 hours. The supernatant was removed to leave the resulting crystal. DMSO was added to dissolve the crystal, and the absorbance of the solution was measured at 540 nm. $IC_{50}$ value was calculated using a computer system according to the following formula:

$(OD_{540}(test)-OD_{540}(blank)/OD_{540}(control)-OD_{540}(blank))\times100$

In the above formula, the $IC_{50}$ value is defined as the concentration of the active compound when the number of cells per well at the end of constant temperature-treatment is 50% of the number of cells in the control medium.

The IC50 values [μg/ml] in the following Table 1 were obtained for the example compounds according to the present invention.

TABLE 1

| Example No. | IC50 [μg/ml] |
|---|---|
| Imatinib mesylate | 0.54 |
| 5 | 0.006 |
| 6 | <0.10 |
| 7 | <0.01 |
| 8 | <0.01 |
| 9 | <0.01 |
| 12 | 0.21 |
| 13 | 0.304 |
| 24 | <0.01 |
| 30 | <0.01 |

As can be seen in the above Table 1, the existing drug of Imatinib mesylate showed an IC 50 value of 0.54 μg/ml against the CML cell line, K562, whereas the compounds of Examples 5, 6, 7, 8, 9, 24, and 30 of the present invention showed an IC50 value of 0.01 μg/ml or less, which corresponds to 50 times improved activity. Further, the compounds of Examples 12 and 13 showed much higher activity than Imatinib mesylate.

Experiment 2

In the present experiment, the inhibitory activity of the compounds of formula (1) was determined against the growth of CT-26 cancer cell. The test was performed according to the same procedure as Experiment 1. Thus obtained IC50 values [μg/ml] are represented in the following Table 2.

TABLE 2

| Example No. | IC50 [μg/ml] |
|---|---|
| Imatinib mesylate | 30.0 |
| 5 | 0.06 |
| 6 | <0.01 |
| 7 | <0.01 |
| 8 | <0.01 |
| 9 | <0.01 |
| 12 | 2.93 |
| 13 | 3.77 |
| 24 | 0.0023 |
| 30 | 0.0094 |

As can be seen in the above Table 2, the existing drug of Imatinib mesylate showed an IC 50 value of 30.00 μg/ml against the leukemia cell line, CT-26, whereas the compounds of Examples 5, 6, 7, 8, 9, 24, and 30 of the present invention showed 300 times improved activity at the same concentration. Further, all the other example compounds showed much higher activity than Imatinib mesylate.

Experiment 3

In the present experiment, the inhibitory activities of Imatinib mesylate and the compounds of Examples 5 and 6 were determined against the growth of several cancer cells. The test was performed according to the same procedure as Experiment 1. Thus obtained IC50 values [μg/ml] are represented in the following Table 3.

TABLE 3

| Cancer Cell | Imatinib mesylate | Example 5 | Example 8 |
|---|---|---|---|
| A549 | 37.18 | 0.082 | 2.23 |
| Panc-1 | 53.05 | 7.1 | 0.498 |
| A-172 | 44.5 | <0.01 | <0.01 |
| RPMI-6666 | 33.76 | <0.01 | <0.01 |
| HT-1197 | 55 | 0.063 | — |
| SNU-C1 | 30 | <0.01 | <0.01 |
| SNU-1 | 32.58 | <0.01 | <0.01 |

As can be seen in the above Table 3, the compounds of Examples 5 and 8 according to the present invention showed improved activity against lung cancer cell of A549, pancreatic cancer cell of PANC-1, encephalophyma cell of A172, lymphoma cell of RPMI-6666, bladder cancer cell of HT-1197, colon cancer cell of SNU-C1, and gastric cancer cell of SNU-1 by the minimum of 15 times to the maximum of 50 times or more, compared with Imatinib mesylate, respectively.

Therefore, it is anticipated that a new therapeutic agent may be developed against these cancers as well as chronic or acute leukemia.

Experiment 4

In the present experiment, the inhibitory activities of Imatinib mesylate, cisplatin, and the compound of Example 8 were determined against the growth of Sarcoma, oral epithelial cancer cell, ovarian cancer cell, lung cancer cell, gastric cancer cell. The test was performed according to the same procedure as Experiment 1. Thus obtained $IC_{50}$ values [μg/ml] are represented in the following Table 5.

TABLE 4

|  | Cisplatin | Imatinib mesylate | Example 8 |
|---|---|---|---|
| Sarcoma-180 | <0.0001 | 53.05 | <0.0001 |
| KB | 0.00028 | 58.57 | 0.00058 |
| SK-OV-03 | 0.782 | 30 | 2.390 |
| A549 | 0.679 | 7.27 | 2.230 |
| SNU-1 | 2.064 | 46.9 | 0.270 |

As can be seen in the above Table 4, the compound of Example 8 according to the present invention showed improved activity against, Sarcoma of Sarcoma-180 and oral epithelial cancer cell of KB, by more than $1\times10^4$ time, respectively, than Imatinib mesylate, and against, gastric cancer cell of SNU-1, ovarian cancer cell of SK-OV-03 and lung cancer cell of A549, by more than 170, 12, 3.5 times, respectively, than Imatinib mesylate.

In the comparison experiment with cisplatin, the compound of Example 8 showed a similar activity against Sarcoma of Sarcoma-180 and oral epithelial cancer cell of KB, and improved activity against gastric cancer cell of SNU-1 by more than 8 times.

Therefore, it is anticipated that a new therapeutic agent may be developed against these cancers as well as chronic or acute leukemia.

Experiment 5

Comparative Pharmacokinetic Test in White Rats

On the previous day to the test, white rats (Sprague-Dawley, 250~280 g, male) were put under anesthesia by pentobarbital sodium (50 mg/kg, I.P.). Then, cannula (polyethylene tube; diameter: 0.58 mm) was introduced into the rats via the carotid artery and jugular vein, and drawn out to the back. After the operation, the rats were fasted for 16 hours and used for the test. Blood was collected in 0, 0.5, 1, 1.5, 2, 2.5, 3, 3.5, 4, 4.5, 5, 6, 8, 10, 12, and 24 hours from the carotid artery. The samples for HPLC analysis were prepared using the collected blood according to the following procedure and were analyzed under the following conditions.

Preparation of the Samples for HPLC Analysis

Blood was collected by an amount of 0.8 ml at each prearranged time and centrifuged at 15,000 rpm for 7 minutes to separate 300 μl of plasma. In order to remove proteins, MeOH was added in an amount of 600 μl, twice as much as the amount of plasma, and the mixture was shaken for 30 minutes. The mixture was centrifuged again at 15,000 rpm for 5 minutes to give protein free supernatant, which was then analyzed by HPLC.

HPLC Analysis Conditions of Example 5

Flow rate: 1.0 ml/min, UV detection at 267 nm
Column: 4.6×150 mm, 5C18-AR-II, COSMOSIL
Eluent: Mixture of ion pair sample (420ml) and MeOH (580ml)
Ion pair sample: 7.5 g of 1-octanesulfonic acid was dissolved in 800 ml of water. The resulting mixture was adjusted to pH 2.5 using phosphoric acid and diluted with water to 1000 ml volume.

HPLC Analysis Conditions of Example 8

Flow rate: 1.5 ml/min, UV detection at 271 nm
Column: 4.6 I.D. ×250 mm, Capcell Pak Phenyl UG120
Eluent: Acetonitrile: 0.2% Formic acid in water (75:25)

When Imatinib mesylate and the compounds of Examples 5 and 8 were administered per oral to the white rats in a dosage of 100 mg/kg, respectively, it was confirmed by the HPLC analysis that Cmax (maximum blood concentration) and AUC (area under the curve of time-blood concentration) of the compound of Example 5 were about 4 times and 5 times, respectively as much as those of Imatinib mesylate. In addition, it was confirmed by the HPLC analysis that Cmax and AUC of the compound of Example 8 were about 1.5 times and 3 times, respectively as much as those of Imatinib mesylate. Here, the pharmacokinetic parameters are Tmax (time to reach the maximum blood concentration), Cmax (maximum blood concentration), and AUC (area under the curve of time-blood concentration), and the AUC was calculated under trapezoid rule (see Table 5 and FIG. 1).

TABLE 5

|  | Imatinib mesylate (100 mg/kg, P.O.) | Example 5 (100 mg/kg, P.O.) | Example 8 (100 mg/kg, P.O.) |
|---|---|---|---|
| Tmax (hr) | 2.3 | 11.2 | 12 |
| Cmax (μg/ml) | 2.724 | 8.27 | 4.1 |
| AUC | 26.461 | 114.47 | 61.33 |

Figure 1:
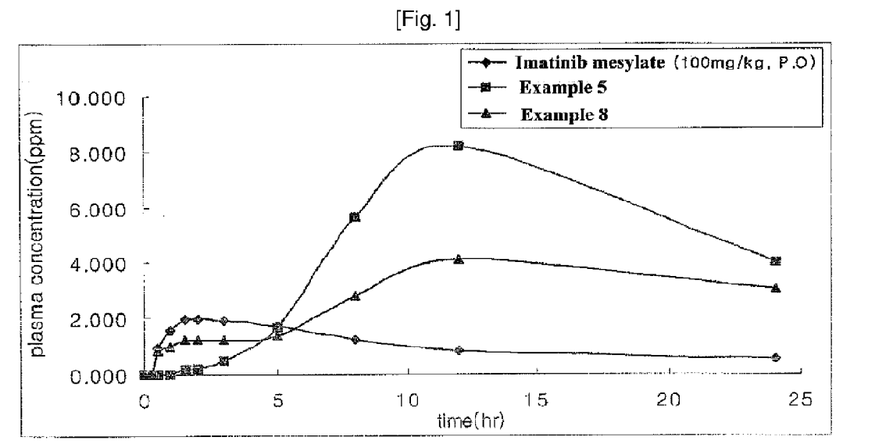
FIG. 1 shows the pharmacokinetic data of the compounds of Examples 5 and 8 according to the present invention compared with a standard drug of Imatinib mesylate.

As shown in the above Table 5, although the concentration of administration of Examples 5 and 8 is the same as that of Imatinib mesylate, it was identified that their pharmacokinetic parameters of Tmax, Cmax, and AUC are higher than those of Imatinib mesylate (Table 5 and FIG. 1). On the basis of these results, it may be concluded that the compounds of Examples 5 and 8 exhibit the same effect as Imatinib mesylate when they are clinically applied at about half lower daily dosage than that of Imatinib mesylate. Therefore, the compound of the present invention has a superior therapeutic effect and various advantages in cost, etc., and also can be formulated into an oral dosage form (tablet or capsule) or an injection form when industrially manufactured.

Experiment 6

Acute Toxicity Test in Mice (Oral Administration)

In order to determine the acute toxicity of the compound of the present invention when the compound is orally administered, mice (ICR, 24~26 g) were fasted for 16 hours. One group consists of 10 males and 10 females. The first group is the control group and 0.5% sodium carboxymethyl cellulose (CMC) was administered per oral to this group. The compounds of Examples 5 and 8 were orally administered in a dosage of 2,000 mg/kg, the maximum dosage in acute toxicity test, to each test group. After the administration, clinical conditions of the mice were observed for 14 days and weight change was also measured. On the last day of the test, 14$^{th}$ day from the start, the mice were subjected to an autopsy in order to examine changes of the internal organs. During the period of observation, neither abnormal response nor specific autopsy result was observed. Also, the body weights of the test groups do not show any change with statistical significance when compared with the control group. Further, since no mouse died during the test period, it was confirmed that the compounds of Examples 5 and 8 have $LD_{50}$ of 2,000 mg/kg or more. This means that the compounds of the present invention including those of Examples 5 and 8 are safe in the aspect of acute toxicity.

Acute toxicity test in rat (oral administration)

In this test, the acute toxicity of the compound of the present invention when the compound is intravenously administered was determined on rat (SD-Rat, 100~110 g). One group consists of 5 males and 5 females. The first group is the control group and 0.5% CMC was intravenously administered to this group. The compounds of Examples 5 and 8 were orally administered in a dosage of 1,000, 2,000 mg/kg, respectively, to each test group. After the administration, clinical conditions of the mice were observed for 14 days and weight change was also measured. On the last day of the test, 14$^{th}$ day from the start, the rat were subjected to an autopsy in order to examine changes of the internal organs. During the period of observation, neither abnormal response nor specific autopsy result was observed. Also, the body weights of the test groups do not show any change with statistical significance when compared with the control group. Further, since no mouse died during the test period, it was confirmed that the compounds of Examples 5 and 8 have $LD_{50}$ of 2,000 mg/kg or more. This means that the compounds of the present invention including those of Examples 5 and 8 are safe in the aspect of acute toxicity.

The invention claimed is:

1. N-phenyl-2-pyrimidine-amine compound represented by the following formula (1):

(1)

or its salt, in which $R_1$ represents optionally substituted thiazole, imidazole or pyrazine
(wherein the substituent is amino group or lower alkyl);

$R_2$, $R_3$ and $R_6$ each independently represent hydrogen, halogen, lower alkyl or lower alkoxy;

$R_4$ and $R_5$ each independently represent hydrogen and $R_4$ and $R_5$ are not simultaneously hydrogen; or $R_4$ or $R_5$ each represents a radical having the following formula (2):

(2)

wherein $R_7$ represents lower alkyl or lower alkyl substituted with 1 to 3 halogen, $R_8$ represents aliphatic having 5 to 10 carbon atoms, or represents optionally substituted 5 to 7 membered saturated or unsaturated monocyclic radical (wherein the substituent is lower alkyl), or bi- or tri-cyclic radical optionally combined with a benzene ring(s), each of which has 1 to 3 hetero atoms selected from a group consisting of nitrogen, oxygen and sulfur, or represents piperazinyl or homopiperazinyl each of which is substituted by lower alkyl.

2. The compound of claim 1 wherein $R_1$ represents pyrazine, 2-methylpyrazine or thiazole;

$R_4$ or $R_5$ represents a radical having the following formula (2):

(2)

wherein $R_7$ represents trifluoromethyl or methyl, $R_8$ represents 2-methylimidazole, 4-methylimidazole.

3. The compound of claim 1 wherein the compound is 4-methyl-N-[3-(4-methylimidazol-1-yl)-5-trifluoromethyl-phenyl]-3-(4-thiazol-2-yl-pyrimidin-2-ylamino)-benzamide;

4-methyl-N-[3-(2-methylimidazol-1-yl)-5-trifluoromethyl-phenyl]-3-(4-thiazol-2-yl-pyrimidin-2-ylamino)-benzamide;

4-methyl-N-(5-methylthiazol-2-yl)-3-(4-thiazol-2-yl-pyrimidin-2-ylamino)-benzamide;

4-methyl-N-[3-(4-methylimidazol-1-yl)-5-trifluoromethyl-phenyl]-3-(4-pyrazin-2-yl-pyrimidin-2-ylamino)-benzamide;

4-methyl-N-[3-(2-methylimidazol-1-yl)-5-trifluoromethyl-phenyl]-3-(4-pyrazin-2-yl-pyrimidin-2-ylamino)-benzamide;

4-methyl-N-[3-(4-methylimidazol-1-yl)-5-trifluoromethyl-phenyl]-3-[4-(3-methylpyrazin-2-yl)-pyrimidin-2-ylamino]-benzamide;

4-methyl-N-[3-(2-methylimidazol-1-yl)-5-trifluoromethyl-phenyl]-3-[4-(3-methylpyrazin-2-yl)-pyrimidin-2-ylamino]-benzamide; or

N-[3-(4-methylimidazol-1-yl)-5-trifluoromethyl-phenyl]-4-(4-thiazol-2-yl-pyrimidin-2-ylamino)-benzamide 2 hydrochloride.

4. The compound of claim 1, wherein R1 represents pyrazine, 2-methylpyrazine or thiazole, R2, R3, R5, R6 each independently represent hydrogen, R4 represents a radical of formula (2), R7 represents trifluoromethyl or methyl, and R8 represents 2-methylimidazole or 4-methylimidazole.

5. The compound of claim 1, wherein R1 represents pyrazine, 2-methylpyrazine or thiazole, R2 represents methyl R3, R4, R6 each independently represent hydrogen, R5 represents a radical of formula (2), R7 represents trifluoromethyl or methyl, and R8 represents 2-methylimidazole or 4-methylimidazole.

6. A process for preparing the compound of formula (1) as defined in claim 1, which comprises reacting a compound represented by the following formula (4a) or (4b):

(4a)

(4b)

wherein $R_1$ to $R_6$ are as defined in claim 1, with a compound represented by the following formula (5):

(5)

wherein $R_7$ to $R_8$ are as defined in claim 1, to produce a compound represented by the following formula (1a) or (1b):

(1a)

(1b)

wherein R1 to R8 are as defined in claim 1.

7. A pharmaceutical composition comprising an effective amount of the compound of formula (1) or its salt as defined in any one of claim 1 to 3 as an active ingredient together with pharmaceutically acceptable inert carriers.

* * * * *